United States Patent
Cone et al.

(10) Patent No.: US 12,138,004 B2
(45) Date of Patent: *Nov. 12, 2024

(54) METHODS FOR ACTIVELY ENGAGING AND DISENGAGING TELEOPERATION OF A SURGICAL ROBOTIC SYSTEM

(71) Applicant: Verb Surgical Inc., Santa Clara, CA (US)

(72) Inventors: Taylor Joseph Cone, Belmont, CA (US); Joan Savall, Palo Alto, CA (US); Anette Lia Freiin von Kapri, Mountain View, CA (US); Eric Mark Johnson, Pacific Grove, CA (US)

(73) Assignee: Verb Surgical Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/418,109

(22) Filed: Jan. 19, 2024

(65) Prior Publication Data

US 2024/0156557 A1 May 16, 2024

Related U.S. Application Data

(63) Continuation of application No. 17/962,766, filed on Oct. 10, 2022, now Pat. No. 11,903,667, which is a (Continued)

(51) Int. Cl.
*A61B 34/00* (2016.01)
*A61B 34/30* (2016.01)
(Continued)

(52) U.S. Cl.
CPC .............. *A61B 34/74* (2016.02); *A61B 34/25* (2016.02); *A61B 34/35* (2016.02);
(Continued)

(58) Field of Classification Search
None
See application file for complete search history.

(56) References Cited

U.S. PATENT DOCUMENTS 7,865,266 B2  1/2011  Moll et al.
8,831,782 B2  9/2014  Itkowitz
(Continued)

FOREIGN PATENT DOCUMENTS

CN   101193603 A   6/2008
CN   102958464 A   3/2013
(Continued)

OTHER PUBLICATIONS

Camarillo et al., "Robotic Technology in Surgery: Past, Present and Future", Departments of Mechanical Engineering, Computer Science and Surgery, Stanford University, Stanford, CA, 2004, 43 pages.

(Continued)

*Primary Examiner* — Jaime Figueroa
*Assistant Examiner* — Arslan Azhar
(74) *Attorney, Agent, or Firm* — Aikin & Gallant, LLP

(57) ABSTRACT

A method for engaging and disengaging a surgical instrument of a surgical robotic system including receiving a sequence of user inputs from one or more user interface devices of the surgical robotic system; determining, by one or more processors communicatively coupled to the user interface devices and the surgical instrument, whether the sequence of user inputs indicates an intentional engagement or disengagement of a teleoperation mode in which the surgical instrument is controlled by user inputs received from the user interface devices; in response to determining of engagement, transition the surgical robotic system into the teleoperation mode; and in response to determining of disengagement, transition the surgical robotic system out of (Continued)

the teleoperation mode such that the user interface devices are prevented from controlling the surgical instrument.

20 Claims, 9 Drawing Sheets

Related U.S. Application Data continuation of application No. 16/236,163, filed on Dec. 28, 2018, now Pat. No. 11,478,318.

(51) Int. Cl.
*A61B 34/35* (2016.01)
*B25J 15/00* (2006.01)
*G06F 3/033* (2013.01)
*G06F 3/0346* (2013.01)
*G06F 3/0354* (2013.01)

(52) U.S. Cl.
CPC ..... *B25J 15/0019* (2013.01); *A61B 2034/301* (2016.02); *A61B 34/76* (2016.02); *G06F 3/0334* (2013.01); *G06F 3/0346* (2013.01); *G06F 3/03547* (2013.01)

(56) References Cited

U.S. PATENT DOCUMENTS

| | | | |
|---|---|---|---|
| 9,314,306 B2 | 4/2016 | Yu | |
| 9,360,934 B2 | 6/2016 | Ruiz et al. | |
| 9,699,445 B2 | 7/2017 | Hoffman et al. | |
| 9,901,402 B2 | 2/2018 | Itkowitz et al. | |
| 9,925,662 B1 | 3/2018 | Jules et al. | |
| 10,251,713 B2 | 4/2019 | Ruiz et al. | |
| 10,895,757 B2 | 1/2021 | Fuerst et al. | |
| 10,980,610 B2 | 4/2021 | Rosenberg et al. | |
| 11,204,640 B2 | 12/2021 | Freiin et al. | |
| 11,224,489 B2 | 1/2022 | Ruiz et al. | |
| 11,333,899 B2 | 5/2022 | Fuerst et al. | |
| 11,337,767 B2 | 5/2022 | Savall et al. | |
| 11,478,318 B2 | 10/2022 | Cone et al. | |
| 2008/0181452 A1 | 7/2008 | Kwon et al. | |
| 2009/0315827 A1 | 12/2009 | Elvesjoe et al. | |
| 2011/0118748 A1 | 5/2011 | Itkowitz | |
| 2012/0071892 A1 | 3/2012 | Itkowitz et al. | |
| 2012/0078080 A1 | 3/2012 | Foley et al. | |
| 2014/0024889 A1 | 1/2014 | Xiaoli | |
| 2015/0080909 A1 | 3/2015 | Itkowitz et al. | |
| 2015/0314447 A1 | 11/2015 | Zhang et al. | |
| 2016/0242860 A1 | 8/2016 | Diolaiti et al. | |
| 2016/0346053 A1 | 12/2016 | Beira | |
| 2016/0361125 A1 | 12/2016 | Balicki et al. | |
| 2017/0172675 A1 | 6/2017 | Jarc et al. | |
| 2017/0180720 A1 | 6/2017 | Jarc | |
| 2018/0016110 A1 | 1/2018 | Nobe et al. | |
| 2018/0036088 A1 | 2/2018 | Kilroy et al. | |
| 2018/0078034 A1 | 3/2018 | Savall et al. | |
| 2018/0078319 A1 | 3/2018 | Nobles et al. | |
| 2018/0092706 A1 | 4/2018 | Anderson et al. | |
| 2018/0161108 A1 | 6/2018 | Savall et al. | |
| 2018/0280099 A1 | 10/2018 | Cone et al. | |
| 2018/0364810 A1 | 12/2018 | Parshionikar | |
| 2019/0076199 A1 | 3/2019 | Kline et al. | |
| 2019/0231456 A1 | 8/2019 | Ruiz et al. | |
| 2019/0298481 A1 | 10/2019 | Rosenberg et al. | |
| 2019/0328473 A1 | 10/2019 | Chassot et al. | |
| 2020/0015918 A1 | 1/2020 | Payyavula et al. | |
| 2020/0038124 A1 | 2/2020 | Lin et al. | |
| 2020/0093367 A1 | 3/2020 | Dory et al. | |
| 2020/0163732 A1 | 5/2020 | Hasser et al. | |
| 2020/0222138 A1 | 7/2020 | Diolaiti | |
| 2020/0315721 A1 | 10/2020 | Rabindran et al. | |
| 2020/0360097 A1 | 11/2020 | Dimaio et al. | |
| 2020/0363868 A1 | 11/2020 | Freiin et al. | |
| 2020/0390510 A1 | 12/2020 | Thompson et al. | |
| 2021/0088807 A1 | 3/2021 | Fuerst et al. | |
| 2021/0145526 A1 | 5/2021 | Robinson et al. | |
| 2021/0145532 A1 | 5/2021 | Tucker et al. | |
| 2022/0179483 A1 | 6/2022 | Freiin et al. | |
| 2024/0024051 A1 | 1/2024 | Tokarchuk et al. | |

FOREIGN PATENT DOCUMENTS

| | | | |
|---|---|---|---|
| CN | 105877846 A | 8/2016 | |
| CN | 106659540 A | 5/2017 | |
| CN | 107331146 A | 11/2017 | |
| CN | 107847283 A | 3/2018 | |
| CN | 107847284 A | 3/2018 | |
| CN | 108472097 A | 8/2018 | |
| CN | 109475387 A | 3/2019 | |
| EP | 3395251 A1 | 10/2018 | |
| JP | 2007-290096 A | 11/2007 | |
| KR | 10-1802464 B1 | 11/2017 | |
| WO | 2018/057814 A1 | 3/2018 | |
| WO | 2018/162921 A1 | 9/2018 | |
| WO | 2018/165047 A1 | 9/2018 | |
| WO | 2018/195319 A1 | 10/2018 | |
| WO | 2018/217444 A2 | 11/2018 | |

OTHER PUBLICATIONS

Extended European Search Report for European Application No. 18945174.3 mailed Oct. 27, 2022, 9 pages.
Final Office Action of the U.S. Patent Office dated Feb. 22, 2022 for related U.S. Appl. No. 16/236,163.
Final Office Action of the U.S. Patent Office dated May 25, 2021 for related U.S. Appl. No. 16/415,974.
Final Office Action of the U.S. Patent Office dated May 3, 2021 for related U.S. Appl. No. 16/236,163.
First Office Action for Chinese Application No. 201980096511.9, mailed Oct. 28, 2023.
International Preliminary Report on Patenlability for International Application No. PCT/US2019/034721 mailed Dec. 2, 2021, 9 pages.
International Preliminary Report on Patentability for International Application No. PCT/US2019/034722 mailed Dec. 2, 2021, 9 pages.
International Preliminary Report on Patentability for International Application No. PCT/US2019/068221 mailed Jul. 8, 2021, 8 pages.
International Search Report & Written Opinion of the PCT Patent Office dated Feb. 3, 2020 for related PCT Patent Application. No. PCT/US2019/034721.
International Search Report & Written Opinion of the PCT Patent Office dated Feb. 6, 2020 for related PCT Patent Application. No. PCT/US2019/034722.
International Search Report and Written Opinion dated Sep. 23, 2019 for related PCT Appln. No. PCT/US2018/068221 18 Pages.
Jack Lloyd, How to Sync a PS3 Controller. Sep. 18, 2018, Accessed through: https://www.wikihow.com/Sync-a-PS3-Controller (Year: 2018).
Latif et al., "Teleoperation through Eye Gaze (TeleGaze): A Multimodal Approach", Published in: 2009 IEEE International Conference on Robotics and Biomimetics (ROBIO), Dec. 2009, 6 Pages.
Non-Final of the U.S. Patent Office dated Jan. 12, 2021 for related U.S. Appl. No. 16/415,974.
Non-Final Office Action of the U.S. Patent Office dated Dec. 14, 2020 for related U.S. Appl. No. 16/236,163.
Non-Final Office Action of the U.S. Patent Office dated Oct. 6, 2021 for related U.S. Appl. No. 16/415,992.
Non-Final Office Action of the U.S. Patent Office dated Oct. 7, 2021 for related U.S. Appl. No. 16/236,163.
Notice of Allowance of the U.S. Patent Office dated Aug. 13, 2021 for related U.S. Appl. No. 16/415,974.
Notice of Allowance of the U.S. Patent Office dated Jan. 26, 2022 for related U.S. Appl. No. 16/415,992, mailed on Jan. 26, 2022, 8 pages.
Notice of Allowance of the U.S. Patent Office dated Jun. 10, 2022 for related U.S. Appl. No. 16/236,163.

(56) References Cited

OTHER PUBLICATIONS

Notice of Allowance of the U.S. Patent Office dated Mar. 18, 2022 for related U.S. Appl. No. 16/415,992.
Notice of Allowance of the USPTO mailed Jan. 26, 2022 for related U.S. Appl. No. 16/415,792.
Office Action received for Chinese Patent Application No. 201880100540.3, mailed on Nov. 27, 2023, 27 pages (16 pages of English Translation and 11 pages of Original Document).
Office Action received for Chinese Patent Application No. 201980096510.4, mailed on Dec. 26, 2023, 27 pages (14 pages of English Translation and 13 pages of Original Document).
Second Office Action for Chinese Patent Application No. 201880100540.3 mailed Jun. 1, 2024 17 pages.

METHODS FOR ACTIVELY ENGAGING AND DISENGAGING TELEOPERATION OF A SURGICAL ROBOTIC SYSTEM

CROSS-REFERENCE TO RELATED APPLICATIONS

This application is a continuation of pending U.S. patent application Ser. No. 17/962,766, filed Oct. 10, 2022, which is a continuation of U.S. patent application Ser. No. 16/236,163, filed Dec. 28, 2018, now U.S. Pat. No. 11,478,318, issued Oct. 25, 2022, which are incorporated herein in their entirety.

BACKGROUND

Field

Embodiments related to robotic systems are disclosed. More particularly, embodiments related to surgical robotic systems and corresponding methods for engaging and disengaging a teleoperation mode of the surgical robotic system, are disclosed.

Background

Endoscopic surgery involves looking into a patient's body and performing surgery inside the body using endoscopes and other surgical tools. For example, laparoscopic surgery can use a laparoscope to access and view an abdominal cavity. Endoscopic surgery can be performed using manual tools and/or a surgical robotic system having robotically-assisted tools.

A surgical robotic system may be remotely operated by a surgeon to command a robotically-assisted tool located at an operating table. Such operation of a robotically-assisted tool remotely by a surgeon may be commonly referred to as teleoperation. For example, the surgeon may use a computer console located in the operating room, or it may be located in a different city, to command a robot to manipulate the surgical tool mounted on the operating table. The robotically-controlled surgical tool can be an endoscope mounted on a robotic arm. Accordingly, the surgical robotic system may be used by the remote surgeon to perform an endoscopic surgery.

The surgeon may provide input commands to the surgical robotic system, and one or more processors of the surgical robotic system can control system components in response to the input commands. For example, the surgeon may hold in her hand a user input device such as a joystick or a computer mouse that she manipulates to generate control signals to cause motion of the surgical robotic system components, e.g., an actuator, a robotic arm, and/or a surgical tool of the robotic system.

SUMMARY

A surgical robotic system may be considered to have various system modes. The primary operation mode may be referred to herein as a teleoperation mode. The surgical robotic system is considered to be in the teleoperation mode when the user is actively controlling, or is able to actively control, the surgical robotic system components, e.g., an actuator, a robotic arm, a surgical tool and/or endoscope, for example, with a user interface device or foot pedal. On the other hand, when the user is unable to actively control the surgical robotic system components, the system is considered to have exited the teleoperation mode, be out of the teleoperation mode, be in a non-teleoperation mode or have disengaged the teleoperation mode. For example, the system may be considered to have exited or disengaged the teleoperation mode or be in a non-teleoperation mode when (1) no user input is accepted by the surgical robotic system, (2) user input commands to a graphical user interface (GUI) of the system are accepted, but cannot control the associated surgical robotic system components or (3) the user is not yet able to control the surgical robotic components, but a sequence of intentional actions would cause the user to enter or engage teleoperation mode. In a teleoperated surgical robotic system, it is important to provide the user with a safe, yet simple, way to actively engage the teleoperation mode to avoid harm due to unintentional tool movement. In addition, it is desirable to provide the user with a way to safely disengage from the teleoperation mode at any time the user actively wants to disengage or performs an action that makes teleoperation anything other than the primary focus. While the surgical robotic system may include various safety requirements to prevent unintentional operations, they may not cover the specific operation of engaging and/or disengage a teleoperation mode and/or may be overly complex and therefore difficult for the user to remember and/or follow.

The instant invention is therefore directed to a surgical robotic system which can detect an intentional user action, a sequence of intentional user actions or a set of intentional user actions, and based on that detection, automatically engage or disengage the teleoperation mode. Representatively, in one aspect, a sequence of intentional user actions or set of intentional user actions are detected by the user interface device. For example, the sequence of intentional user action(s) may be a predetermined set of gestures detected by the user interface device, such as the user tapping on the user interface device or squeezing the user interface device. Alternatively, the intentional action(s) may be an action which results in the user interface device being in a particular location, orientation and/or position, such as the user docking the user interface device in a docking station or positioning the user interface in close proximity to the docking station. Still further, the action(s) could be an action relating to a foot pedal of the surgical robotic system, alone, or in combination with, the previously discussed actions in connection with the user interface device. For example, the action(s) or set of actions could include tapping the clutch pedal or pressing and holding the clutch pedal, in combination with a tapping and/or squeezing of the user interface device.

Representatively, in one aspect, the user interface device may be a handheld user input or interface device that includes a grip that a surgeon can manipulate using her hand, to generate an input command to move an actuator, to which a robotic surgical tool and/or end effector is coupled in the surgical robotic system. The surgeon can move the grip within a workspace, such as a range of motion of a linkage system connected to the grip, to remotely cause a corresponding movement of the actuator when in the teleoperation mode. When a limit of the workspace is reached, e.g., when the linkage system is fully extended, the surgeon can press a clutch button or finger clutch so that the input from the surgical robotic system does not cause movement of the actuator and, in turn, the robotic surgical tool and/or end effector is paused or otherwise remains in the current position. That is, when the finger clutch is pressed, the grip can be repositioned within the workspace without causing a corresponding movement of the actuator, robotic surgical tool and/or end effector, which would otherwise occur if the finger clutch were not pressed. In order to actuate the finger clutch, the surgeon must apply a force large enough to counter a return spring force of the clutch. For example, the surgeon must press downward on the finger clutch. When the surgeon releases this downward pressure on the finger clutch, the robotic surgical tool and/or end effector is no longer paused in the current position and the user can continue a movement of the actuator and associated components using the user interface device. It should be understood, however, that the single action of pressing/holding of the finger clutch to pause the associated robotic surgical component in the current position, or releasing of the finger clutch to continue movement of the component, should not be understood as an intentional sequence of user actions which can be used to disengage the teleoperation mode. Rather, the clutching or pausing of the associated robotic surgical component, in comparison to disengaging the teleoperation mode, is a more temporary operation, which is caused by a relatively simple user action. In particular, during a clutching operation, a signal from the user interface device to the actuator, robotic surgical tool and/or end effector to move the actuator, robotic surgical tool and/or end effector is temporarily suspended, or overridden by a clutch signal to pause the operation, but once a single action occurs, for example the user removing their finger from the finger clutch, the desired movement can continue. In contrast, when teleoperation mode is disengaged, for example in response to the previously discussed intentional action(s) by the user, the user interface device may be considered permanently disconnected from the actuator, tool and/or end effector. For example, when teleoperation mode is disengaged, the signal from the user interface device may no longer be transmitted to the actuator, robotic surgical tool, and/or end effector, and/or the user interface device may remain disconnected until a relatively complex, and intentional, sequence of actions is performed by the user. The intentional sequence of actions are actions which indicate a user's intention to engage teleoperation mode and may be more complex than a single action used for clutching or pausing the system. In other words, the system will not engage (or disengage) teleoperation mode upon detecting a single action used for clutching. Rather, an intentional sequence of actions must be detected for the system to re-engage the teleoperation mode, and in turn, reconnect the user interface device with the actuator, tool and/or end effector. In other words, in contrast the clutching operation, simply removing the first action will not automatically reconnect the user interface device with the actuator, tool and/or end effector. Rather, another intentional action, which in some cases may be the same as the first intentional action (i.e., symmetrical actions), is required to reconnect the user interface device to the actuator, tool and/or end effector, and therefore engage the teleoperation mode.

More specifically, in one aspect, the invention is directed to a method for engaging and disengaging a surgical instrument of a surgical robotic system. The method may include receiving a sequence of user inputs from one or more user interface devices of the surgical robotic system. The method may further include determining, by one or more processors communicatively coupled to the user interface devices and the surgical instrument, whether the sequence of user inputs indicates an intentional engagement or disengagement of a teleoperation mode in which the surgical instrument is controlled by user inputs received from the user interface devices. In response to determining of engagement, the surgical robotic system may transition into the teleoperation mode; and in response to determining of disengagement, the surgical robotic system may transition out of the teleoperation mode such that the user interface devices are prevented from controlling the surgical instrument. The user interface devices may include at least one of a handheld user input device and a foot pedal. The sequence of user inputs indicating an engagement or disengagement of the teleoperation mode may be different. In other cases, the sequence of user inputs indicating an engagement or disengagement of the teleoperation mode may be the same. In some cases, the sequence of user inputs may include a first sequence of user inputs from a first user interface device and a second sequence of user inputs from a second user interface device. In still further aspects, the one or more user interface devices may include a handheld user input device and a clutch pedal, and the sequence of user inputs comprise a first sequence of user inputs received from the handheld user input device and a second sequence of user inputs received from the clutch pedal. In some aspects, the sequence of user inputs indicating an intentional engagement or disengagement may correspond to pressing and holding a clutch pedal of the one or more user interface devices and double tapping a finger clutch of the one or more user interface devices. Still further, the sequence of user inputs indicating an intentional engagement or disengagement may correspond to pressing and holding a clutch pedal of the one or more user interface devices and squeezing another of the one or more user interface devices. Still further, the sequence of user inputs indicating an intentional engagement or disengagement may correspond to double tapping a clutch pedal of the one or more user interface devices. The method may further include determining whether at least one of the following conditions are met prior to transitioning the surgical robotic system into a teleoperation mode: a chair of the surgical robotic system is locked, a user is looking at a screen of the surgical robotic system, and the user interface device is within a surgical robotic system workspace. The method may further include a user feedback for alerting the user that the teleoperation mode is engaged or disengaged.

In another aspect, the invention is directed to a surgical robotic system including a surgical instrument, a user console comprising a user interface device and a foot pedal, the user interface device being mechanically ungrounded with respect to the user console and one or more processors communicatively coupled to the surgical instrument and the user console. The processors may be configured to receive a sequence of user actions through the user interface device and/or the foot pedal, determine that the surgical robotic system is in a non-teleoperation mode and the sequence of user actions indicate an intentional engagement, and transition the surgical robotic system into a teleoperation mode in which the surgical instrument is controlled by user inputs received from the user interface device and the foot pedal. In one aspect, the user interface device may include a first handheld user input device and a second handheld user input device, and the sequence of user actions indicating an intentional engagement comprise tapping or squeezing both the first and the second handheld user input devices. In another aspect, the foot pedal may be a clutch pedal, and the sequence of user actions indicating an intentional engagement comprise pressing and holding the clutch pedal, and tapping or squeezing the user interface device, or the sequence of user actions indicating an intentional engagement comprise tapping the clutch pedal, and tapping or squeezing the user interface device.

In another aspect, the surgical robotic system may include a surgical instrument, a user console comprising a user interface device and a foot pedal, the user interface device being mechanically ungrounded with respect to the user console, and one or more processors communicatively coupled to the surgical instrument and the user console. In this aspect, the processors may be configured to receive a sequence of user actions through the user interface device and/or the foot pedal, determine that the surgical robotic system is in a teleoperation mode and the sequence of user actions indicate an intentional disengagement, wherein the surgical instrument is controlled by user inputs received from the user interface device and the foot pedal in the teleoperation mode, and transition the surgical robotic system into a non-teleoperation mode in which the user interface device or the foot pedal is prevented from controlling the surgical instrument. In one aspect, the foot pedal is a clutch pedal and the sequence of user actions indicating an intentional disengagement comprise double tapping the clutch pedal. In another aspect, the sequence of user actions indicating an intentional disengagement may include pressing and holding the clutch pedal, and tapping a finger clutch of the user interface device, or pressing and holding the clutch pedal, and squeezing the user interface device. In still further aspects, the user interface device is a handheld user input device comprising a sensor operable to detect the user inputs, and at least one of the user inputs comprise a docking of the portable handheld user interface device.

The above summary does not include an exhaustive list of all aspects of the present invention. It is contemplated that the invention includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

The embodiments of the invention are illustrated by way of example and not by way of limitation in the figures of the accompanying drawings in which like references indicate similar elements. It should be noted that references to "an" or "one" embodiment of the invention in this disclosure are not necessarily to the same embodiment, and they mean at least one. Also, in the interest of conciseness and reducing the total number of figures, a given figure may be used to illustrate the features of more than one embodiment of the invention, and not all elements in the figure may be required for a given embodiment.

DETAILED DESCRIPTION

Embodiments describe processes for engaging and disengaging a teleoperation mode based on user actions in connection with, for example, a user interface device (UID) usable by a robotic system to control actuators that move a robotic arm or a tool. The robotic system can be a surgical robotic system, the robotic arm can be a surgical robotic arm, and the tool can be a surgical tool. The UID may, however, be used by other systems, such as interventional cardiology systems, vision systems, or aircraft systems, to control other output components. These other systems name only a few possible applications.

In various embodiments, description is made with reference to the figures. However, certain embodiments may be practiced without one or more of these specific details, or in combination with other known methods and configurations. In the following description, numerous specific details are set forth, such as specific configurations, dimensions, and processes, in order to provide a thorough understanding of the embodiments. In other instances, well-known processes and manufacturing techniques have not been described in particular detail in order to not unnecessarily obscure the description. Reference throughout this specification to "one embodiment," "an embodiment," or the like, means that a particular feature, structure, configuration, or characteristic described is included in at least one embodiment. Thus, the appearance of the phrase "one embodiment," "an embodiment," or the like, in various places throughout this specification are not necessarily referring to the same embodiment. Furthermore, the particular features, structures, configurations, or characteristics may be combined in any suitable manner in one or more embodiments.

The use of relative terms throughout the description may denote a relative position or direction. For example, "distal" may indicate a first direction away from a reference point, e.g., away from a user. Similarly, "proximal" may indicate a location in a second direction opposite to the first direction, e.g., toward the user. Such terms are provided to establish relative frames of reference, however, and are not intended to limit the use or orientation of, for example a UID, to a specific configuration described in the various embodiments below.

Figure 1:
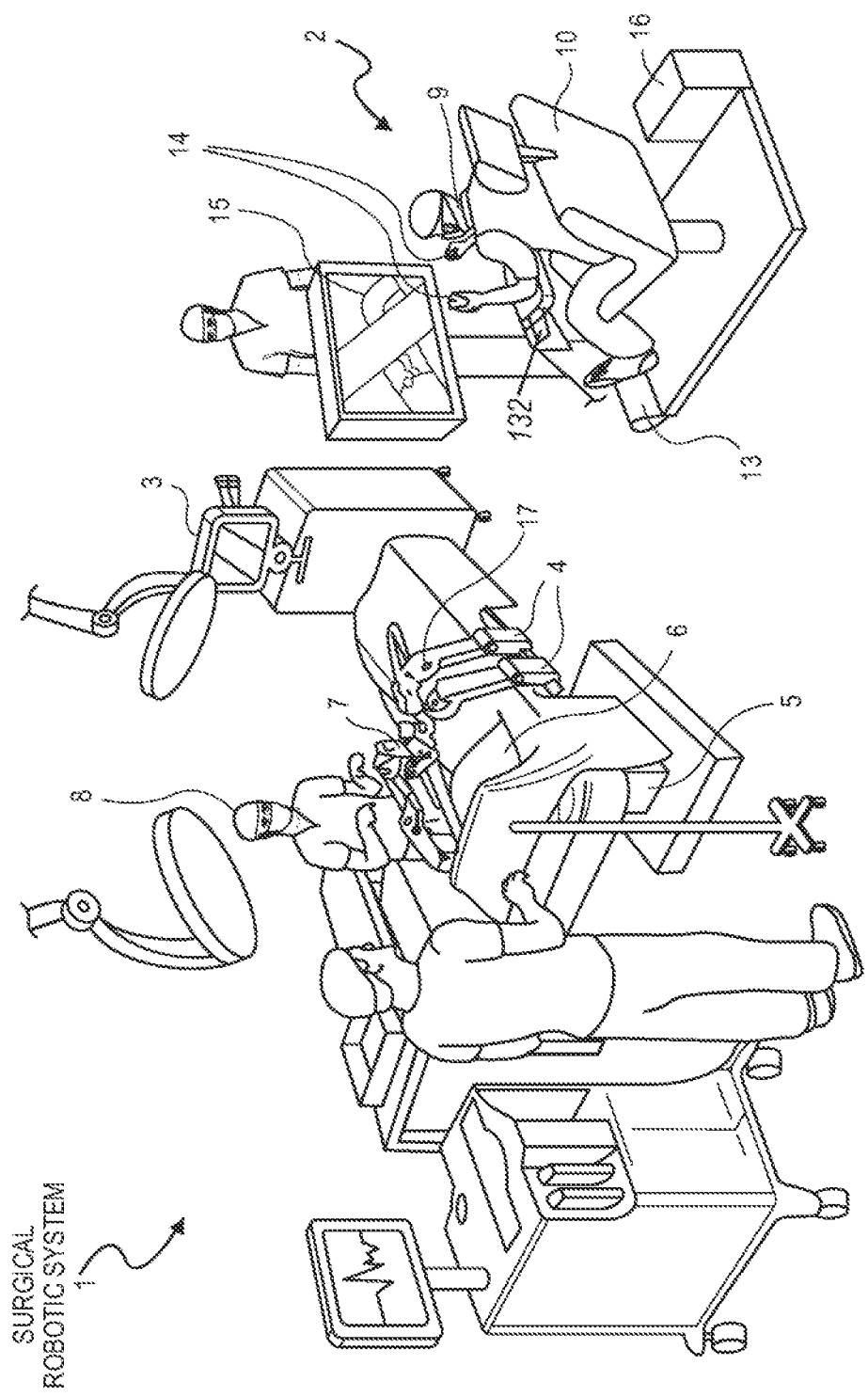
FIG. 1 is a pictorial view of an example surgical robotic system in an operating arena, in accordance with an embodiment.

Referring to FIG. 1, this is a pictorial view of an example surgical robotic system 1 in an operating arena. The robotic system 1 includes a user console 2, a control tower 3, and one or more surgical robotic arms 4 at a surgical robotic platform 5, e.g., a table, a bed, etc. The system 1 can incorporate any number of devices, tools, or accessories used to perform surgery on a patient 6. For example, the system 1 may include one or more surgical tools 7 used to perform surgery. A surgical tool 7 may be an end effector that is attached to a distal end of a surgical arm 4, for executing a surgical procedure.

Each surgical tool 7 may be manipulated manually, robotically, or both, during the surgery. For example, the surgical tool 7 may be a tool used to enter, view, or manipulate an internal anatomy of the patient 6. In an embodiment, the surgical tool 7 is a grasper that can grasp tissue of the patient. The surgical tool 7 may be controlled manually, by a bedside operator 8; or it may be controlled robotically, via actuated movement of the surgical robotic arm 4 to which it is attached. The robotic arms 4 are shown as a table-mounted system, but in other configurations the arms 4 may be mounted in a cart, ceiling or sidewall, or in another suitable structural support.

Generally, a remote operator 9, such as a surgeon or other operator, may use the user console 2 to remotely manipulate the arms 4 and/or the attached surgical tools 7, e.g., teleoperation. The user console 2 may be located in the same operating room as the rest of the system 1, as shown in FIG. 1. In other environments however, the user console 2 may be located in an adjacent or nearby room, or it may be at a remote location, e.g., in a different building, city, or country. The user console 2 may comprise a seat 10, foot-operated controls 13, one or more handheld user input or interface devices, UID 14, and at least one user display 15 that is configured to display, for example, a view of the surgical site inside the patient 6. In the example user console 2, the remote operator 9 is sitting in the seat 10 and viewing the user display 15 while manipulating a foot-operated control 13 and a handheld UID 14 in order to remotely control the arms 4 and the surgical tools 7 (that are mounted on the distal ends of the arms 4.)

In some variations, the bedside operator 8 may also operate the system 1 in an "over the bed" mode, in which the beside operator 8 (user) is now at a side of the patient 6 and is simultaneously manipulating a robotically-driven tool (end effector as attached to the arm 4), e.g., with a handheld UID 14 held in one hand, and a manual laparoscopic tool. For example, the bedside operator's left hand may be manipulating the handheld UID to control a robotic component, while the bedside operator's right hand may be manipulating a manual laparoscopic tool. Thus, in these variations, the bedside operator 8 may perform both robotic-assisted minimally invasive surgery and manual laparoscopic surgery on the patient 6.

During an example procedure (surgery), the patient 6 is prepped and draped in a sterile fashion to achieve anesthesia. Initial access to the surgical site may be performed manually while the arms of the robotic system 1 are in a stowed configuration or withdrawn configuration (to facilitate access to the surgical site). Once access is completed, initial positioning or preparation of the robotic system 1 including its arms 4 may be performed. Next, the surgery proceeds with the remote operator 9 at the user console 2 utilizing the foot-operated controls 13 and the UIDs 14 to manipulate the various end effectors and perhaps an imaging system, to perform the surgery. Manual assistance may also be provided at the procedure bed or table, by sterile-gowned bedside personnel, e.g., the bedside operator 8 who may perform tasks such as retracting tissues, performing manual repositioning, and tool exchange upon one or more of the robotic arms 4. Non-sterile personnel may also be present to assist the remote operator 9 at the user console 2. When the procedure or surgery is completed, the system 1 and the user console 2 may be configured or set in a state to facilitate post-operative procedures such as cleaning or sterilization and healthcare record entry or printout via the user console 2.

In one embodiment, the remote operator 9 holds and moves the UID 14 to provide an input command to move a robot arm actuator 17 in the robotic system 1. The UID 14 may be communicatively coupled to the rest of the robotic system 1, e.g., via a console computer system 16. The UID 14 can generate spatial state signals corresponding to movement of the UID 14, e.g., position and orientation of the handheld housing of the UID, and the spatial state signals may be input signals to control a motion of the robot arm actuator 17. The robotic system 1 may use control signals derived from the spatial state signals, to control proportional motion of the actuator 17. In one embodiment, a console processor of the console computer system 16 receives the spatial state signals and generates the corresponding control signals. Based on these control signals, which control how the actuator 17 is energized to move a segment or link of the arm 4, the movement of a corresponding surgical tool that is attached to the arm may mimic the movement of the UID 14. Similarly, interaction between the remote operator 9 and the UID 14 can generate, for example a grip control signal that causes a jaw of a grasper of the surgical tool 7 to close and grip the tissue of patient 6.

The UID 14 may also be provided to command other operations by surgical robotic system 1. For example, UID 14 may include a finger clutch, as described below, and pressing on the finger clutch may generate a clutch signal to pause the motion of actuator 17 corresponding to the surgical robotic arm 4 and surgical tool 7. For example, when a user presses the finger clutch of UID 14 with a finger, the finger clutch may generate a clutch signal, and the clutch signal may be an input signal to pause all motion of actuator(s) 7, and correspondingly, all motion of surgical robotic arm 4 and surgical tool 7. When all motion of surgical robotic arm 4 and surgical tool 7 are paused, there is no movement in any direction and no change in orientation of surgical robotic arm 4 and surgical tool 7. The clutch signal may be termed a "clutch activation signal" when the assertion of the signal pauses motion of actuator(s) 7. Similarly, the input signal may be a "clutch deactivated signal" when no touch by operator 9 is detected, and motion of actuator(s) 7 is not paused. The clutch signal, e.g., the clutch activation signal, when asserted, can pause motion of the robotic arm and surgical tool regardless of the spatial state signals. Accordingly, the clutch signal effectively overrides the actuation command that is derived from the spatial state signals.

In addition, the UID 14 may be used to detect an intentional user action, sequence of intentional user actions or set of intentional user actions, indicating a desire by the user to engage or disengage the teleoperation mode. For example, UID 14 may detect a tap, double tap, squeeze, or other gesture associated with the UID 14, and the system may be programed to recognized one or more of these intentional user action(s) as a command to engage or disengage a teleoperation mode and, in turn, send an engage or disengage signal to the surgical robotic system to engage or disengage teleoperation mode. In one embodiment, the intentional action(s) which are required to disengage or engage the teleoperation mode, may be the same, or otherwise considered symmetrical actions. For example, double tapping on the finger clutch can, when not in teleoperation mode, be used to engage teleoperation mode, and double tapping of the finger clutch can, when in teleoperation mode, be used to disengage teleoperation mode. In other cases, the intentional actions used to engage or disengage teleoperation mode may be different (e.g., asymmetrical). In addition, in some cases, the intentional user action(s) may include positioning the UID 14 in (or at least near) docking station 132, or may be intentional user action(s) with respect to another input device of the surgical robotic system 1. For example, the foot-operated control(s) 13 may include a clutch pedal, and tapping the clutch pedal, alone or in combination with any of the previously discussed intentional actions may cause the surgical robotic system to engage and/or disengage from the teleoperation mode. In an embodiment, one or more sensors, for example capacitive sensing pads, may be located on UID 14, foot-operated control(s) 13 (e.g., clutch pedal) and/or docking station 132, and the intentional user action or set of intentional user actions may be detected by the sensing pads, and send an engage and/or disengage signal to one or more processors of the surgical robotic system 1 to engage and/or disengage the teleoperation mode.

The surgical robotic system 1 may include several UIDs 14, where respective control signals are generated for each UID that control the actuators and the surgical tool (end effector) of a respective arm 4. For example, the remote operator 9 may move a first UID 14 to control the motion of an actuator 17 that is in a left robotic arm, where the actuator responds by moving linkages, gears, etc., in that arm 4. Similarly, movement of a second UID 14 by the remote operator 9 controls the motion of another actuator 17, which in turn moves other linkages, gears, etc., of the robotic system 1. The robotic system 1 may include a right arm 4 that is secured to the bed or table to the right side of the patient, and a left arm 4 that is at the left side of the patient. An actuator 17 may include one or more motors that are controlled so that they drive the rotation of a joint of the arm 4, to for example change, relative to the patient, an orientation of an endoscope or a grasper of the surgical tool 7 that is attached to that arm. Motion of several actuator(s) 17 in the same arm 4 can be controlled by the spatial state signals generated from a particular UID 14. The UIDs 14 can also control motion of respective surgical tool graspers. For example, each UID 14 can generate a respective grip signal to control motion of an actuator, e.g., a linear actuator, that opens or closes jaws of the grasper at a distal end of surgical tool 7 to grip tissue within patient 6.

In some aspects, the communication between the platform 5 and the user console 2 may be through a control tower 3, which may translate user commands that are received from the user console 2 (and more particularly from the console computer system 16) into robotic control commands that transmitted to the arms 4 on the robotic platform 5. The control tower 3 may also transmit status and feedback from the platform 5 back to the user console 2. The communication connections between the robotic platform 5, the user console 2, and the control tower 3 may be via wired and/or wireless links, using any suitable ones of a variety of data communication protocols. Any wired connections may be optionally built into the floor and/or walls or ceiling of the operating room. The robotic system 1 may provide video output to one or more displays, including displays within the operating room as well as remote displays that are accessible via the Internet or other networks. The video output or feed may also be encrypted to ensure privacy and all or portions of the video output may be saved to a server or electronic healthcare record system.

It will be appreciated that the operating room scene in FIG. 1 is illustrative and may not accurately represent certain medical practices.

Figure 2:
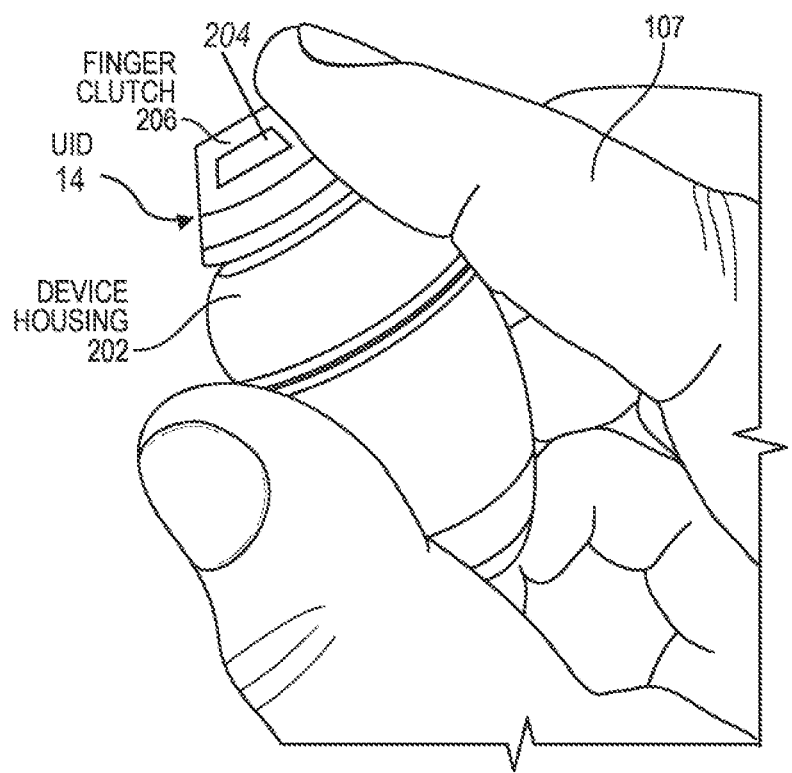
FIG. 2 is a pictorial view of a user interface device having a finger clutch, in accordance with an embodiment.

Referring to FIG. 2, a pictorial view of a UID having a finger clutch is shown in accordance with an embodiment. A UID 14 can include a device housing 202 to be held by an operator or user 107. For example, user 107 may hold device housing 202 between several fingers and move UID 14 within a workspace. The workspace may be a range within reach of user 107. As described below, UID 14 may include a tracking sensor to detect a position and/or orientation of device housing 202 when user 107 moves the UID 14, and the detected position and/or orientation may be correlated to another component of a surgical robotic system. For example, the tracking sensor may detect translation, rotation, or tilting of device housing 202 within the workspace. The tracking sensor may include an accelerometer and/or a gyroscope or other inertial sensors. The movement of UID 14 within the workspace can cause a corresponding movement of a surgical robotic arm, a surgical tool, or an end effector of the surgical tool, e.g., a grasper or a jaw, of the surgical robotic system.

UID 14 may include a clutch mechanism to decouple movement of UID 14 from movement of the surgical robotic arm 112 and/or surgical tool 104. For example, UID 14 can include a finger clutch 206 mounted on device housing 202 to clutch the surgical robotic system. Finger clutch 206 may be so-termed because it may be actuated by a single pressing action, from a finger of user 107. That is, when user 107 presses finger clutch 206 with the finger, the touch may be detected as a clutch input. In response to the clutch input, movement of UID 14 detected by the tracking sensor may not be used by the one or more processors to control movement of the surgical robotic system. When the clutch input is removed (when the touch is ended) the movement of UID 14 may again cause a corresponding movement of the surgical robotic system. That is, when finger clutch 206 is unclutched, e.g., by removing the finger from finger clutch 206, UID 14 movement may again be detected and used by surgical robotic system 1 as a motion control input.

The clutching mechanism of UID 14 can allow user 107 to reposition UID 14 within the workspace when a limit of the workspace has been reached. For example, by extending an arm fully from a start position in a direction while holding UID 14, user 107 may reach the limit of the workspace, e.g., an edge of the workspace. To reposition UID 14 within the workspace and allow for additional movement in the direction of the workspace edge, user 107 can press finger clutch 206 with an index finger to disconnect the robotic system from the movement of UID 14. User 107 may then move UID 14 back to the start position within the workspace and unclutch the surgical robotic system 1 by lifting the index finger from finger clutch 206. Additional movement in the first direction may then be performed by moving UID 14 to command movement of surgical robotic arm 112.

In addition, UID 14 may also include a sensor 204, or sensing portion, for detecting the intentional user actions, sequence of intentional user actions or set of intentional user actions, for engaging and/or disengaging teleoperation mode. Sensor 204 may, in some embodiments, be positioned within, along, on, or otherwise near, finger clutch 206 such that it is easily reachable by the user's finger. For example, sensor 204 could be a pressure sensor, or conductive sensor, located within, along, on, or otherwise near, finger clutch 206. Representatively, sensor 204 may be part of an outer touch surface of finger clutch 206 that faces outward toward a surrounding environment. When a finger of user 107 touches outer touch surface of finger clutch 206, the finger is separated from a conductive pad within finger clutch 206 by a wall thickness of the clutch cover. Clutch cover may be formed from a dielectric material, e.g., a plastic, and thus, a capacitance across the wall of the finger clutch cover will change when the conductive finger of user 107 touches outer touch surface.

Figure 3:
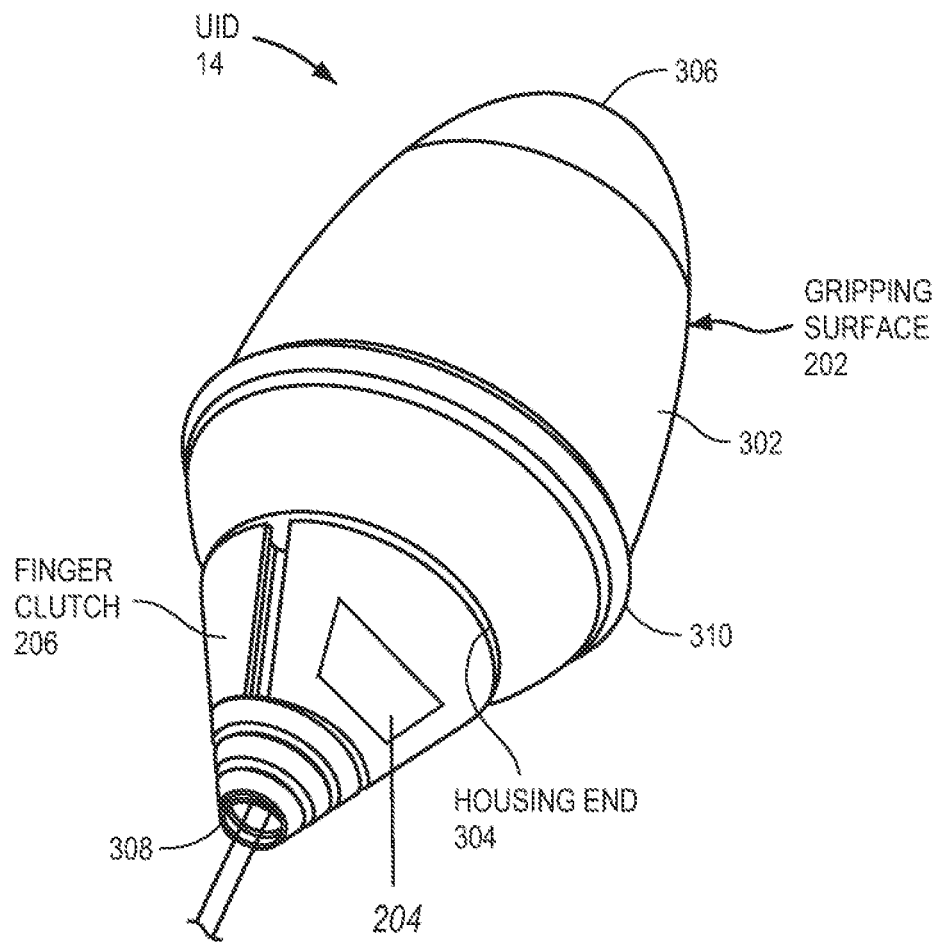
FIG. 3 is a perspective view of a user interface device, in accordance with an embodiment.

Referring to FIG. 3, a perspective view of a UID is shown in accordance with an embodiment. From this view, it can be seen that device housing 202 of UID 14 may further include a gripping surface 302 to be held between several fingers of user 107. Device housing 202 can have one or more rounded or bulbous surface contours. For example, device housing 202 may be generally ovoid or egg-shaped, or it may be an ellipsoid. In an embodiment, a portion of device housing 202 in front of a circumferential ridge 310 of device housing 202 may be shorter and have a less gradual contour or taper than a portion of device housing 202 in back of ridge 310.

In an embodiment, finger clutch 206 is mounted on a housing end 304. For example, housing end 304 may be a distal end of the device housing 202. Housing end 304 can be a location or surface that is at an extremity of housing 202 in a first longitudinal direction. For example, the location can be an edge of housing 202 that is farthest from an opposite end of housing, e.g., a proximal end 306.

Finger clutch 206 may extend distally from housing end 304. Locating finger clutch 206 at a front part of UID 14 may allow user 107 to easily reach forward and touch finger clutch 206, and in turn allow sensor 204 to detect such a touch, with an index finger while holding gripping surface 302 between a thumb and another finger. Accordingly, UID 14 may be sized and shaped to be comfortably held within a hand of user 107. Command signals input through UID 14 may be communicated to computer system 16 through a wired or, more preferably, a wireless connection.

Representatively, in some embodiments, UID 14 may be a portable handheld user input device or controller that is ungrounded with respect to another component of the surgical robotic system. For example, UID 14 may be ungrounded while either tethered or untethered from the user console. The term "ungrounded" is intended to refer to implementations where, for example, both UIDs are neither mechanically nor kinematically constrained with respect to the user console. For example, a user may hold a UID 14 in a hand and move freely to any possible position and orientation within space only limited by, for example, a tracking mechanism of the user console. Signals (e.g., tracking sensor signals, clutch signals or engage/disengage teleoperation mode signals) may be wirelessly communicated between UID 14 and computer system 16. In addition, a power source, such as a rechargeable battery, may be stored within the housing of UID 14 so that it does not need to be mechanically connected to a power source, such as by a wire or cable. Since UID 14 may be untethered and/or mechanically ungrounded, a remote operator 9 and/or bedside operator 8 can carry UM 14 and move about one Or more locations within the operating arena (e.g., the bedside of the patient 6) during a procedure. In this aspect, UID 14 allows the operator 9 and/or operator 8 to control the arm 4 and/or surgical tool 7 from the one or more locations within the operating arena, for example, various locations near the bedside of patient 6. In addition, while at the bedside, the operator can control the arm 4 and/or surgical tool 7 using the UID 14 and a manual tool, simultaneously. The simultaneous manipulation of the arm 4 and/or surgical tool 7 and a manual tool reduces the need for another operator, for example a surgical assistant, to manipulate the manual tool while the remote operator 9 operates the arm 4 and/or surgical tool 7.

Moreover, the portable handheld 14 would allow the operator 8 or 9 during the course of the surgery to alternate between sitting at console 10 and controlling the arm 7 and/or tool 7, and standing at another location within the operating arena (e.g., near a bedside). For example, for certain surgical procedures, the operator 8 or 9 may find it more comfortable or easier to control his or her movements while sitting at console 10, and for others, better to be near the patient's bedside. The operator can therefore move between various locations and/or positions as a procedure dictates.

In other embodiments, an electrical wire may extend from UID 14 to connect UID 14 to computer system 16 and/or console 10. The electrical wire may provide power to UID 14 and may carry sensor signals, e.g., tracking sensor signals, clutch signals or engage/disengage teleoperation mode signals, to computer system 16. Accordingly, UID 14 may be a peripheral device used to input commands to computer system 16. UIDs 14 can be used in combination with other peripheral input devices. For example, a clutch pedal (e.g., foot-operated control(s) 13) may be connected to computer system 16 to provide a clutch input, or engage/disengage input, to surgical robotic system 1. Whereas each UID 14 may be individually clutched to pause teleoperation of respective surgical robotic arms or surgical tools, the respective surgical robotic arms or tools may also be clutched at a same time by pressing the clutch pedal. Thus, movement of actuators 17 may be commanded by UIDs 14 and other peripheral input devices of computer system 16, such as a clutch pedal operated by a user's foot.

Figure 4:
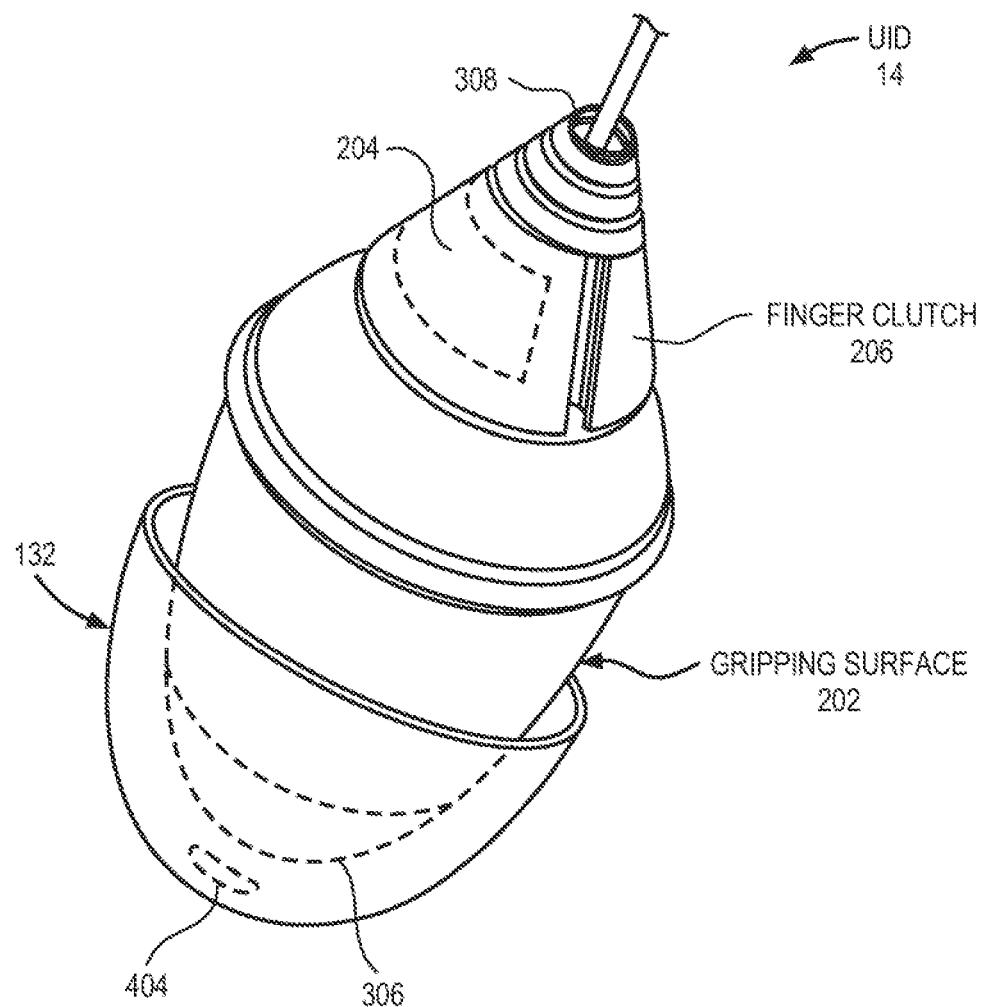
FIG. 4 is a perspective view of a user interface device in a docking station, in accordance with an embodiment.

Referring to FIG. 4, FIG. 4 illustrates a perspective view of a UID in a docking station in accordance with an embodiment. Representatively, docking station 132 may form an interior chamber dimensioned to receive the proximal end 306 of UID 14. In addition, in some embodiments, docking station 132 may further include a docking sensor 404 that detects when the UID 14 is in, or proximal to, docking station 132. For example, docking sensor 404 may be a pressure sensor or capacitive sensor which can detect when UID 14 contacts the surface of docking station 132. In other aspects, sensor 404 could be a sensor that detects when UID 14 is in close proximity to docking station 132, but not necessarily contacting docking station 132. For example, sensor 404 could be a proximity sensor that detects a proximity of UID 14 to docking station 132. In still further cases, UID 14 may include a sensor in addition to, or instead of docking sensor 404, for detecting when UID 14 is in contact with, or in close proximity to, docking station 132. Once docking sensor 404 detects that UID 14 is at docking station 132, docking sensor 404 sends a signal to the surgical robotic system 1 indicating that UID 14 is docked (or nearby and about to be docked), and therefore, for example, teleoperation mode should be disengaged. In addition, docking sensor 404 can also detect when the UID 14 is no longer docked, or no longer near, docking station 132, and therefore send a signal indicating that the user is ready to enter teleoperation mode, and therefore the various components (e.g., actuator, tools and/or end effectors) are ready to be re-engaged.

Figure 5:
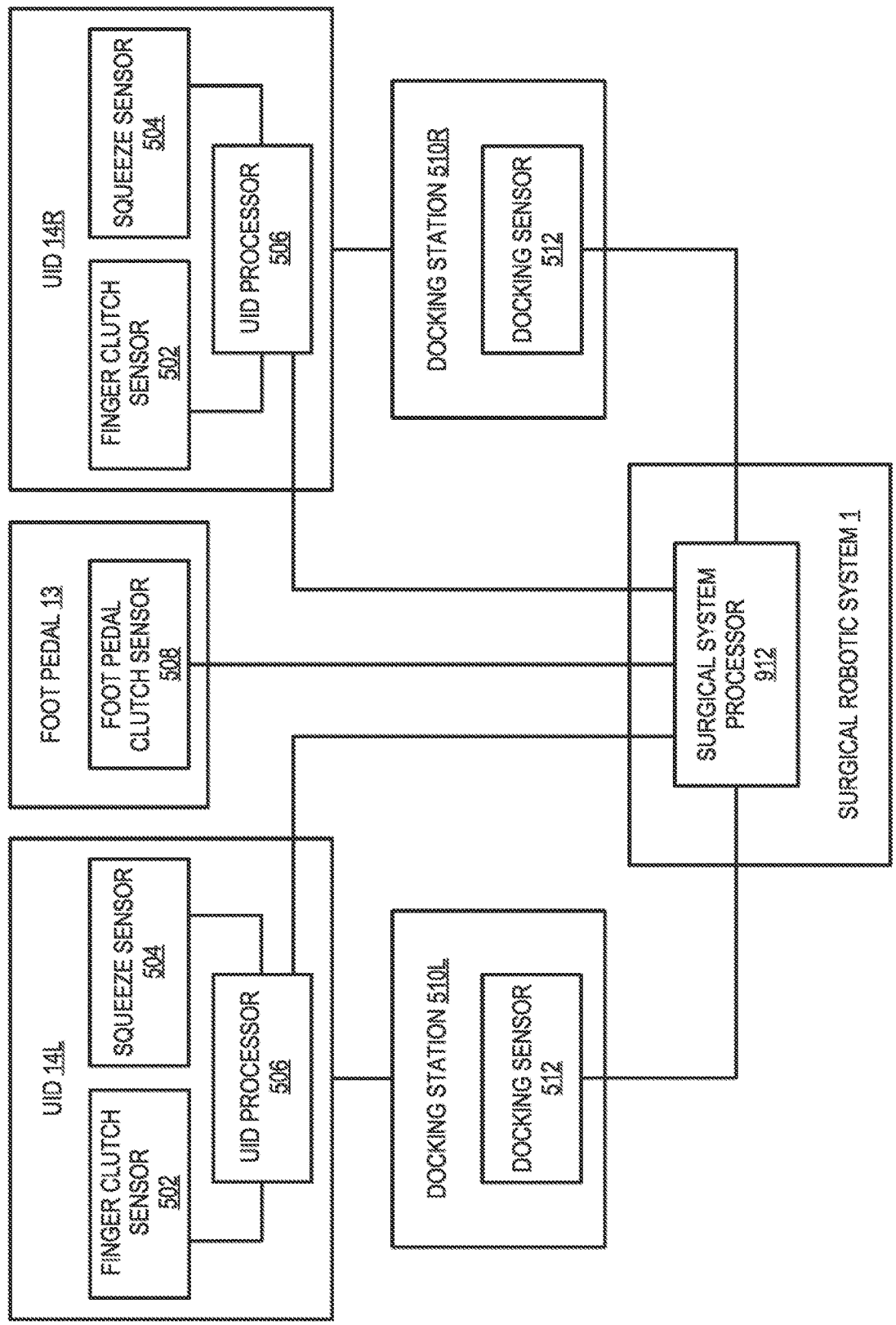
FIG. 5 is a block diagram of a computer portion of a surgical robotic system, in accordance with an embodiment.

FIG. 5 is a block diagram of a computer portion of a surgical robotic system, in accordance with an embodiment. As illustrated in FIG. 5, UID 14 may include UID 14L and UID 14R. UID 14L may be operated by a left hand of a user while UID 14R may be operated by a right hand of the user. For example, UID 14L may be used to control, for example, surgical robotic components to a left side of the patient, and UID 14R may be used to control, for example, surgical robotic components to a right side of the patient, as previously discussed. Each of UID 14L and UID 14R may include an internal volume to receive various electronics and/or other components. For example, each of UID 14L and 14R may include a UID processor 506 mounted within device housing 202. The UID processor 506 may encompass circuitry for analog and digital signal processing, including sensing amplifier circuits and analog to digital conversion circuitry used to interface with the capacitive sensor, and logic circuitry including programmable logic or a programmable digital processor. UID processor 506 may be mounted on a printed circuit board having various sensor terminals to connect UID processor 506 to device sensors, e.g., finger clutch sensor 502 or squeeze sensor 504. A battery (not shown) may be mounted on, or otherwise associated with, the printed circuit board to power electronic components of UID 14L and 14R.

Each of UID 14R and 14L may further include a finger clutch sensor 502. Finger clutch sensor 502 may be substantially the same as, for example, sensor 204 previously discussed in reference to FIG. 4. Representatively, finger clutch sensor 502 may be a sensor that can detect a predetermined intentional user action or set of intentional user actions that indicated a desire by a user to engage or disengage a teleoperation mode. For example, finger clutch sensor 502 may be a capacitive sensor associated with finger clutch 206 that can be actuated when user 107 taps a finger on the finger clutch cover. UID processor 506 may be configured to determine, in response to a change in the capacitance of finger clutch sensor 502, that a predetermined intentional user action (or sequence of intentional user actions) has been performed by user 107. For example, in an embodiment, UID processor 506 may be configured to determine the predetermined intentional user action, sequence of intentional user actions or set of user actions has occurred when the change of capacitance is for a predetermined period of time and/or repeats itself for a predetermined prior of time. For example, the finger clutch sensor 502 may detect a single or double finger tap on finger clutch 206 by user 107, and transmit a corresponding signal to UID processor 506. The single or double tap may be a gesture by user 107 that includes touching the finger on finger clutch sensor 502 for a predetermined period of time (e.g., 0.5 seconds or less) and, in the case of a double tap, at a predetermined interval (e.g., 0.5 seconds or less between taps). When the change of capacitance detected is greater than a predetermined threshold for the predetermined period of time (and/or interval), UID processor 506 can determine that user 107 has performed one of the predetermined intentional actions, or a set of intentional actions, indicating a desire to engage and/or disengage teleoperation mode. Accordingly, UID processor 506, in turn, can generate a corresponding signal that is transmitted to surgical system processor 912 (e.g., computer system 16). Surgical system processor 912 can, in turn, determine whether the signal indicates a desire to engage teleoperation mode or disengage teleoperation mode, for example, based on whether the system is, or is not, already in teleoperation mode. Once the associated command is determined, an engage signal to engage teleoperation mode or a disengage signal to disengage teleoperation mode may be generated, or otherwise initiated by the processor, to cause the surgical robotic system to engage (e.g., enter) or disengage (e.g., exit) the teleoperation mode.

It will be appreciated that finger clutch sensor 502 may be one or more sensor types to detect a touch by user 107. More particularly, although finger clutch sensor 502 has been primarily described as including a capacitive sensor, finger clutch sensor 502 may be a different type of sensor, or combination of sensors, to determine that user 107 has touched finger clutch. For example, finger clutch sensor 502 could include a proximity sensor that can detect a proximity of the finger of user 107 to finger clutch 206, or UID 14L or 14R in general, before it actually contacts the surface. Accordingly, the embodiments described above intended to encompass different types of sensors that detect touch based on a presence or proximity of an object, and in some cases, without requiring the detection of a threshold force applied by the object on finger clutch 206.

UID 14L and 14R may further include a squeeze sensor 504 associated with the device housing 202. In an embodiment, squeeze sensor 504, when squeezed, generates a squeeze signal. More particularly, squeeze sensor 504 is configured to generate a squeeze signal in response to a squeeze on device housing 202. Accordingly, squeeze sensor 504 can detect when user 107 engages in an intentional user action, sequence of intentional user actions or set of intentional user actions that involve squeezing device housing 202 as an indication of the user's desire to engage or disengage teleoperation mode. For example, squeeze sensor 504 may detect when the user 107 squeezes device housing 202 once, or repeatedly squeezes device housing 202. Squeeze sensor 504 may then output a corresponding squeeze signal to UID processor 506, which in turn, transmits a signal to surgical robotic system processor 912. Surgical robotic system processor 912 may then determine whether the squeeze signal indicates a desire by the user to engage and/or disengage a teleoperation mode. For example, when a squeeze is detected for a predetermined period of time (e.g., 0.5 seconds or less), and in the case of a double squeeze, at a predetermined interval (e.g., 0.5 seconds of less between squeezes), the processor will understand this as an intentional user action, sequence of intentional user actions or set of intentional user actions to engage and/or disengage teleoperation mode. In some cases, squeeze sensor 504 may be, or may be associated with, a grip flex circuit which, which, when user 107 squeezes device housing 202, will deform and the physical deformation may be converted into an electrical signal, e.g., a capacitance signal. In other cases, squeeze sensor 504 may be an optical sensor such as a proximity sensor that can detect proximity (or change in distance) to an inner wall of device housing 202. In another example, squeeze sensor 504 may include an ultrasonic sensor, a magnetic sensor, an inductive sensor, or other suitable kind of proximity sensor. In addition, it should be understood that in some embodiments, the user can also squeeze device housing 202 to control a gripping action of an end effector, however, the squeeze associated with a gripping action is different than an intentional single or double squeeze action indicating a desire by the user to engage and/or disengage teleoperation mode, and processor 912 is programmed to distinguish between the two to avoid any unintentional operations.

UID 14 may include other circuitry. For example, UID 14 may include a drop detection sensor to, for example, prevent unintentional instrument movement when UID 14 is dropped. For example, the drop detection sensor can generate a drop signal in response to entering a free fall state when dropped. In an embodiment, the drop detection sensor may be a tracking sensor which monitors movement of UID 14. When the tracking sensor detects movement corresponding to a dropped state, the sensor generates a clutch signal to pause all motion of surgical robotic system 1. In addition, in some embodiments, UID 14 may include a docking sensor. For example, the previously discussed docking sensor 404 may be coupled to UID 14 in addition to, or instead of, docking station 132. The docking sensor may detect when UID 14 is docked, or is otherwise near docking station 132 in a manner that suggests the user is about to dock UID 14.

Alternatively, each of docking stations 510L and 510R associated with respective ones of UID 14L and 14R may include a docking sensor 512. Docking sensor 512 may be substantially the same as docking sensor 404 previously discussed in reference to FIG. 4. For example, docking sensor 512 may be associated (e.g., mounted to) each docking station 510L and 510R, and may detect when a respective one of UID 14L and 14R is positioned within, or proximal to, docking station 510L and 510R. For example, docking sensor 512 may be a pressure sensor or capacitive sensor which can detect when UID 14L or 14R contacts the surface of docking station 510L or 510R. In other aspects, docking sensor 512 could be a sensor that detects when UID 14L or 14R is in close proximity, but not necessarily contacting, docking station 510L or 510R. Once docking sensor 512 detects that UID 14L or 14R is at docking station 510L or 510R, docking sensor 512 sends a signal to surgical system processor 912. Surgical system processor 912 can, in turn, use this information to determine whether this is an intentional user action indicating a desire of the user to engage and/or disengage teleoperation mode. In addition, docking sensor 512 can also detect when the UID 14L or 14R is no longer docked, or no longer near, docking station 510L or 510R, and send a corresponding signal to surgical system processor 912 for use in determining whether to engage and/or disengage teleoperation mode.

The surgical robotic system may further include a foot-operated control such as foot pedal 13. User 107 may use foot pedal 13 to control the surgical robotic components (e.g., actuators, tools and/or end effectors) or to, for example, pause an operation in the case of a clutch pedal, as previously discussed. For example, user 107 may press on foot pedal 13 to control the corresponding surgical robotic component, or pause an operation of a surgical robotic component (in the case of a clutch pedal). In some cases foot pedal 13 may include, or may be, a clutch pedal having a clutch sensor 508, which similar to any of the previously discussed sensors 502, 504 and 512, can be used to detect a predetermined intentional user action or set of intentional user actions indicating a desire by the user 107 to engage or disengage teleoperation mode. In this case, however, the action may be performed with the user's foot. For example, the foot pedal clutch sensor 508 may detect an intentional user action such as a single tap of the user's foot on the clutch pedal, or a double tap of the user's foot on the clutch pedal. For example, when a single foot tap on foot pedal is detected for a predetermined period of time (e.g., 0.5 seconds or less), and in the case of a double tap, at a predetermined interval (e.g., 0.5 seconds of less between taps), the processor will understand this as an intentional user action, sequence of intentional user actions, or set of intentional user actions indicating a desire to engage and/or disengage teleoperation mode. Once detected, foot pedal clutch sensor 508 may send a corresponding signal to the surgical system processor 912, and processor 912 may determine based on the signal and whether, for example, the system is, or is not, already in teleoperation mode, whether to engage and/or disengage teleoperation mode.

Figure 6:
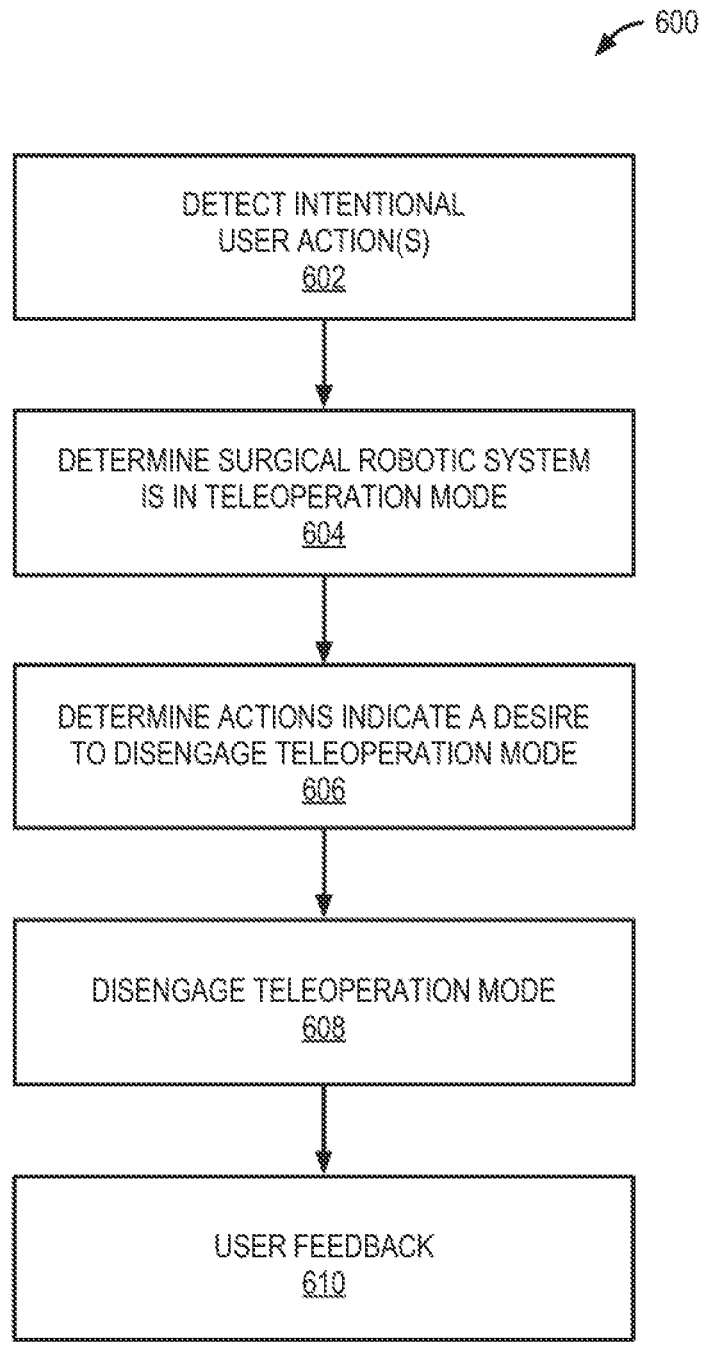
FIG. 6 is a block diagram of an exemplary process for disengaging teleoperation mode, in accordance with an embodiment.
Figure 7:
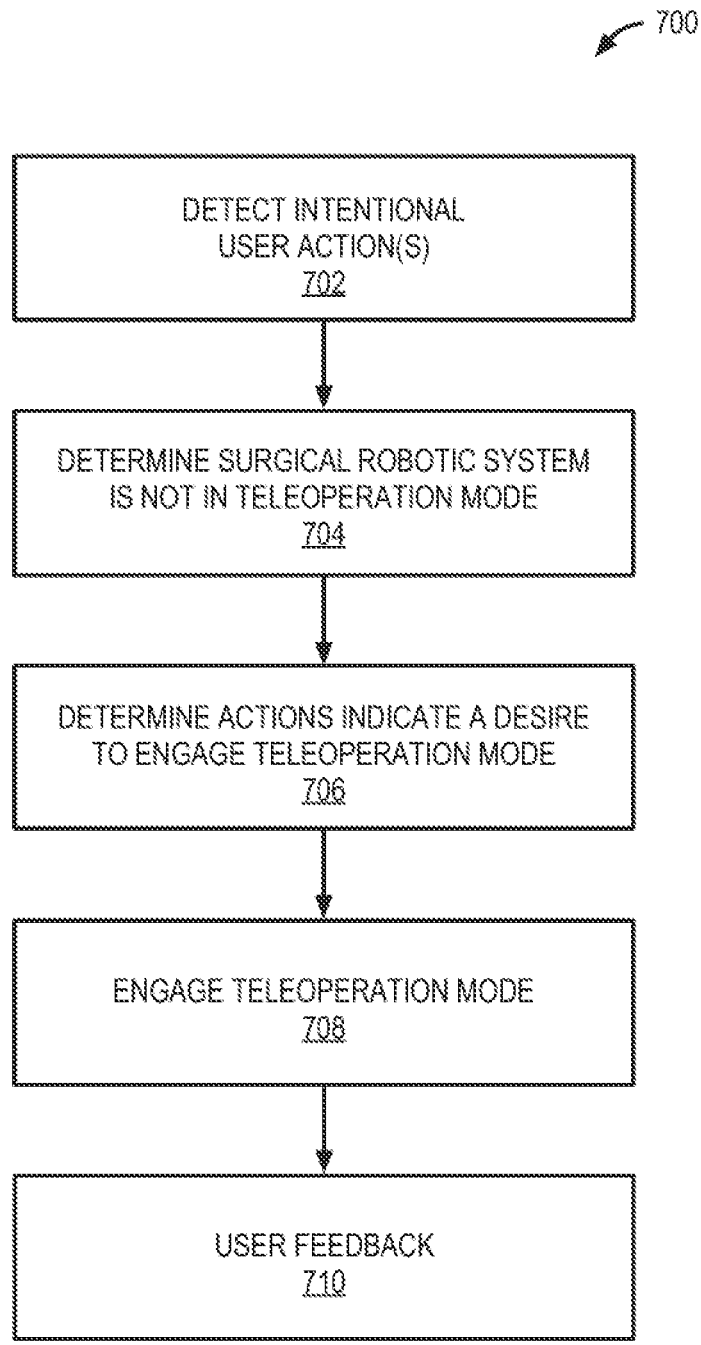
FIG. 7 is a block diagram of an exemplary process for engaging teleoperation mode, in accordance with an embodiment.
Figure 8:
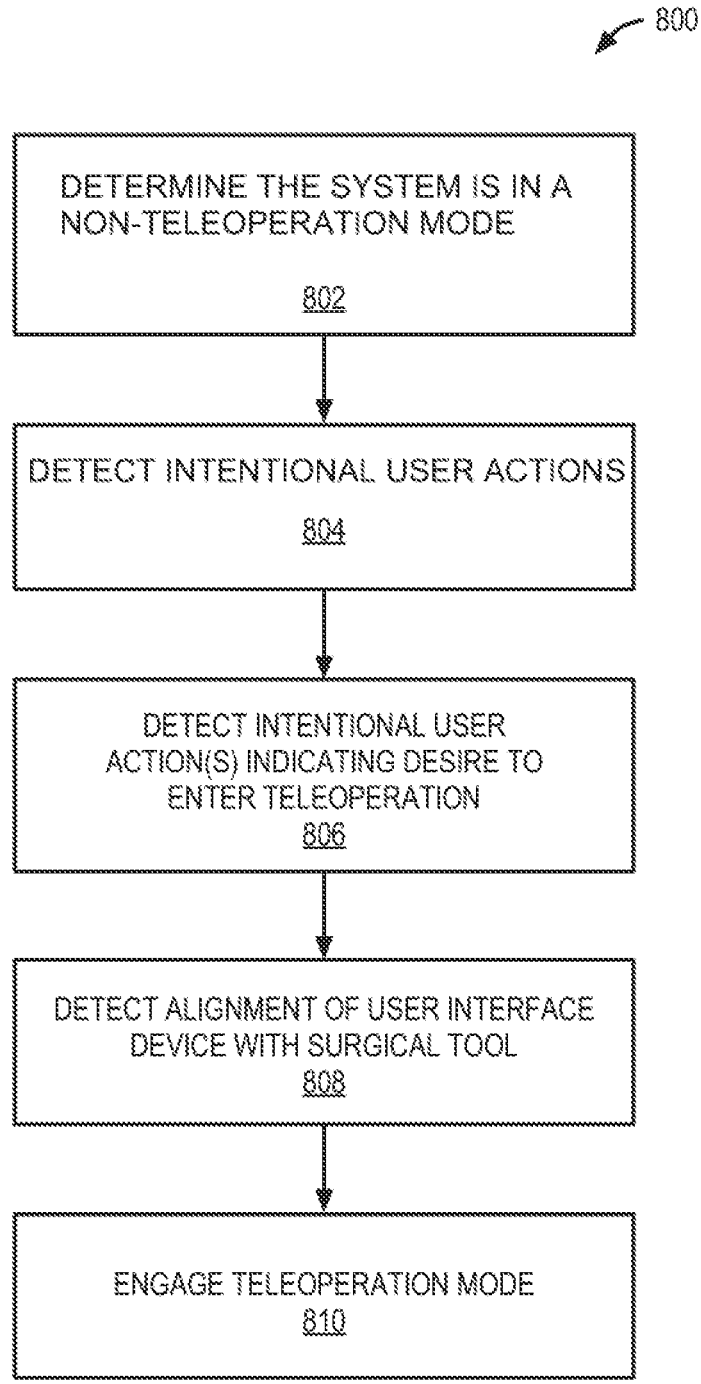
FIG. 8 is a block diagram of an exemplary process for engaging teleoperation mode, in accordance with an embodiment.

The intentional user actions, sequence of intentional user actions or set of intentional user actions, and various combinations, that can be detected by the sensors disclosed herein for determining whether to engage and/or disengage teleoperation mode will now be described in more detail in reference to FIG. 6-FIG. 7. Representatively, FIG. 6 is a block diagram of an exemplary process for disengaging teleoperation mode, and FIG. 7 and FIG. 8 illustrate exemplary processes for engaging teleoperation mode, once an intentional user action or set of intentional user actions are detected. As previously discussed, the intentional user action, sequence of intentional user actions or set of intentional user actions may include a single action, a repeated action, and/or a combination of actions detected by the surgical robotic system, and which are recognized by the surgical robotic system as user commands to engage and/or disengage the teleoperation mode. In addition, in some embodiments, the same sequence of intentional user actions or set of intentional user actions used to, for example, disengage the teleoperation mode, may also be used to engage the teleoperation mode. In this aspect, the intentional user action, sequence of intentional user actions or set of intentional user actions for engaging and/or disengage teleoperation mode may be considered symmetrical actions. In other embodiments, the intentional user action, sequence of intentional user actions or set of intentional user actions by be different, or asymmetrical. It should further be recognized that because both UID 14L and 14R may be mechanically ungrounded, uncoupled or unrestrained, from any other component of the surgical robotic system, the intentional user actions, sequence of intentional user actions or set of intentional user actions, and/or various combinations of actions can be performed easily, and at any number of locations within the surgical arena.

Referring now in more detail to FIG. 6 illustrating a process for disengaging teleoperation mode, process 600 may include the initial operation of detection of an intentional user action(s) (block 602). Representatively, in one embodiment, the intentional sequence of user action(s) detected by the surgical robotic system is a double tap of the UID finger clutch on both UIDs simultaneously. For example, the user may double tap the left UID 14L and the right UID 14R simultaneously, and each double tap may be detected by the corresponding finger clutch sensor 502, associated with each UID 14L and 14R as previously discussed. It should be recognized that the double tap, or other intentional user action(s) detected by the finger clutch sensor 502 to engage or disengage the teleoperation mode, is different than a user input that would cause a clutching operation (e.g., pressing of the finger clutch) to pause the system, as previously discussed.

In another embodiment, the intentional user action(s) detected at operation 502 may be a docking action in which one or more of the UIDs are docked in their respective docking stations or positioned near their respective docking stations. Representatively, docking of both UID 14L and UID 14R, docking one of UID 14L or 14R, or positioning one or both of UIDs 14L and 14R near their respective docking stations 510L and/or 510R, may be the intentional action(s) which is detected and indicates a desire by a user to disengage teleoperation mode. For example, in one aspect, the docking of both UID 14L and 14R (or positioning both UID 14L and 14R near a docking station) may result in the disengagement of teleoperation mode, and all operations that are controlled by the UID 14L and 14R may be prevented. In other embodiments, the docking of one of UID 14L or 14R (or positioning one of UID 14L and 14R near a docking station) may result in the disengagement of teleoperation mode, and all operations that are controlled by the UID 14L and 14R may be prevented. In still further embodiments, docking of only UID 14L (or positioning UID 14L near a docking station) may be used to disengage teleoperation mode with respect to only surgical robotic components controlled by the UID 14L, without disengagement of the teleoperation mode with respect to the surgical robotic components controlled by UID 14R. In other words, the user may continue to operate the surgical robotic components controlled by UID 14R. Similarly, docking of UID 14R (or positioning UID 14R near a docking station) may be used to disengage teleoperation mode with respect to only surgical robotic components controlled by the UID 14R, without disengaging the teleoperation mode with respect to the surgical robotic components controlled by UID 14L. In addition, it should be recognized that the docking of one or both of UID 14L and/or 14R may be used to disengage teleoperation mode of any number of surgical robotic components, for example, one surgical robotic component, two surgical robotic components, three surgical robotic components, or more.

It should further be recognized that although specific intentional user action(s) have been mentioned, it is contemplated that a number of intentional user action(s) and/or combinations of intentional user action(s) with respect to various input devices of the system may be detected in operation 602. Table 1 provides a listing of the predetermined intentional user action(s), sequences of user action(s), sets of intentional user action(s) and/or combinations of intentional user action(s) that may be performed in combination (e.g., in sequence) and detected and recognized by the system as indicating a desire of the user to engage and/or disengage the teleoperation mode.

TABLE 1

Representative Intentional Action(s) for Disengagement of Teleoperation Mode

Single tap clutch pedal
Double tap clutch pedal
Single tap both UID finger clutches
Double tap both UID finger clutches
Single squeeze both UIDs
Double squeeze both UIDs
Dock one UID
Dock both UIDs It should further be understood that in some embodiments, in addition to the previously discussed intentional user action(s), the user may also press and hold the clutch pedal prior to performing any one or more of the action(s). For example, in one embodiment, the user may press and hold clutch pedal, then (1) single tap both finger clutches, (2) double tap both finger clutches, (3) single squeeze both UIDs and/or (4) double squeeze both UIDs. For example, if the user desires to disengage when the UIDS 14L and 14R are at a position/orientation that makes the finger clutch difficult to reach, the user may press and hold the clutch pedal, orient the UIDs for better reachability of the finger clutch, double tap the UID finger clutch (system disengages at this point), and release the clutch pedal.

Returning now to process 600, process 600 may further include the operation of determining that the surgical robotic system is in teleoperation mode (block 604). For example, since as previously discussed, in some embodiments, the intentional user action(s) indicating a desire to disengage teleoperation mode may be the same as those for engagement of teleoperation mode, the current mode of the surgical robotic system may be determined in order to interpret the action(s). Where it is determined the surgical robotic system is in teleoperation mode, the intentional sequence of action(s) are determined to indicate a desire to disengage teleoperation mode in operation 606. Teleoperation mode of the surgical robotic system is then disengaged in operation 608.

In addition, in some embodiments, process 600 includes an optional user feedback operation (block 610), which provides feedback to the user alerting them of a mode transition and/or present operation mode. Representatively, the feedback may be visual (e.g., on-screen or LED lights on display 15 or console 2), auditory (e.g., tones from the surgeon bridge or control tower 130) or haptic (e.g., UID vibrations). For example, when the user disengages teleoperation mode, any one or combination of these feedback systems are possible. For example, a haptic feedback mechanism could be incorporated into one of more of UIDs 14L and 14R, which would give the user a physical sensation that they've disengaged with control of the associated surgical robotic tool. The visual feedback could be an LED light strip on or around display 15, and for example, a green light could indicate the system is disengaged from teleoperation mode, while a red light could indicate the system is engaged in teleoperation mode. Still further, the user could receive an on-screen visual feedback from the graphical user interface (which may involve text, icons, or both) alerting them of the current mode. The notification could automatically disappear after the user completes disengagement of the teleoperation mode, or after a present period of time. Auditory alerts (e.g., beeps, tones, etc.) are further contemplated.

FIG. 7 illustrates a process for engaging teleoperation mode. Process 700 may include the initial operation of detection of an intentional user action(s) (block 702). Representatively, in one embodiment, the intentional user action(s) detected by the surgical robotic system is a double tap of the UID finger clutch on both UIDs simultaneously to engage the teleoperation mode. For example, the user may double tap the left UID 14L and the right UID 14R simultaneously, and each double tap may be detected by the corresponding finger clutch sensor 502, associated with each UID 14L and 14R as previously discussed.

It should further be recognized that although specific intentional user action(s) indicating a desire to engage teleoperation mode have been mentioned, it is contemplated that a number of intentional user action(s) and/or combinations of intentional user action(s) that may be performed in combination (e.g., in sequence) using one or more input devices of the system that may be detected in operation 702. Representatively, in one embodiment, the intentional user action(s) detected by the surgical robotic system may be any one or more of the intentional user actions listed in Table 2.

TABLE 2

Representative Intentional Action(s) for Engagement of Teleoperation Mode

Single tap clutch pedal
Double tap clutch pedal
Single tap both UID finger clutches
Double tap both UID finger clutches
Single squeeze both UIDs
Double squeeze both UIDs It should further be understood that in some embodiments, in addition to the previously discussed intentional user action(s), the user may also press and hold the clutch pedal prior to performing any one or more of the action(s). For example, in one embodiment, the user may press and hold clutch pedal, then (1) single tap both finger clutches, (2) double tap both finger clutches, (3) single squeeze both UIDs and/or (4) double squeeze both UIDs. For example, if the user needs to orient the UIDs 14L and 14R in a specific manner (e.g., to match the tools), the user may also press and hold the clutch pedal, then double tap the UID finger clutch (on one or both of UIDs 14L and 14R), orient the UIDs as desired, and then release the clutch pedal. In addition, in some embodiments, prior to engaging teleoperation mode, the user may be required to perform various unlock gestures, for example using graphical a user interface lock icon, then align UIDs, as will be discussed in more detail in reference to FIG. 8.

Returning now to process 700, process 700 may further include the operation of determining that the surgical robotic system is not in teleoperation mode (block 704). For example, since as previously discussed, in some embodiments, the intentional user action(s) or sequence of intentional user actions indicating a desire to engage teleoperation mode may be the same as those for disengagement of teleoperation mode, the current mode of the surgical robotic system may be determined in order to interpret the action(s). Where it is determined the surgical robotic system is not in teleoperation mode, the intentional sequence of actions are determined to indicate a desire to engage teleoperation mode in operation 706. Teleoperation mode of the surgical robotic system is then engaged in operation 708.

In addition, in some embodiments, process 700 includes an optional user feedback operation (block 710), which provides feedback to the user alerting them of a mode transition and/or present operation mode. Representatively, the feedback may be visual (e.g., on-screen or LED lights on display 15 or console 2), auditory (e.g., tones from the surgeon bridge or control tower 130) or haptic (e.g., UID vibrations). For example, when the user engages teleoperation mode, any one or combination of these feedback systems are possible. For example, a haptic feedback mechanism could be incorporated into one of more of UIDs 14L and 14R, which would give the user a physical sensation that they've engaged with control of the associated surgical robotic tool. The visual feedback could be an LED light strip on or around display 15, and for example, a red light could indicate the system is engaged in teleoperation mode, while a green light could indicate the system is disengaged from teleoperation mode. Still further, the user could receive an on-screen visual feedback from the graphical user interface (which may involve text, icons, or both) alerting the user the system is in teleoperation mode. The notification could automatically disappear after the user completes engagement of the teleoperation mode, or after a present period of time. Auditory alerts (e.g., beeps, tones, etc.) are further contemplated.

In addition, it should be recognized that prior to engaging teleoperation mode, in addition to the intentional user action(s) described herein, there may be additional safety requirements that must be met to ensure it is safe to enter the teleoperation mode. Representatively, the surgical robotic system may further include additional or optional intentional actions, including alignment requirements, that must be met, before engaging teleoperation mode. It is therefore contemplated that in some embodiments, detection of the intentional user action(s) described, for example in reference to operation 700, may occur, for example, after these additional or optional actions occur, and before the final alignment operations. This process is illustrated in more detail in FIG. 8. Representatively, process 800 for engaging teleoperation mode includes determining the surgical robotic system is in a non-teleoperation mode (802), and detect a first set or sequence of intentional user actions (block 804). Representative actions may be, for example, locking the chair, detection of the user looking at a display screen, detecting that the UIDs are not docked, and that the UIDs are in the workspace (e.g., using the tracking system). Next, a second set or sequence of intentional user action(s) indicating a desire to enter teleoperation mode as previously discussed, are detected (block 806). Process 800 further includes the additional operation of detecting alignment of at least one of the UIDs with the corresponding surgical robotic component (e.g., actuator, tool and/or end effector) (block 808). For example, during a surgical operation, a surgical robotic tool may be positioned inside of the body of the patient, and the rotation/orientation of that tool is displayed to the user. Prior to engaging teleoperation, the user must align the rotation/orientation of the UID (he they are held) with the rotation/orientation of the tool within the patient, as viewed on the display. Then, once each of the first intentional user actions and second intentional user action(s) are detected, and alignment operations (e.g., operations 804-808) are met, teleoperation mode is engaged (block 810).

Figure 9:
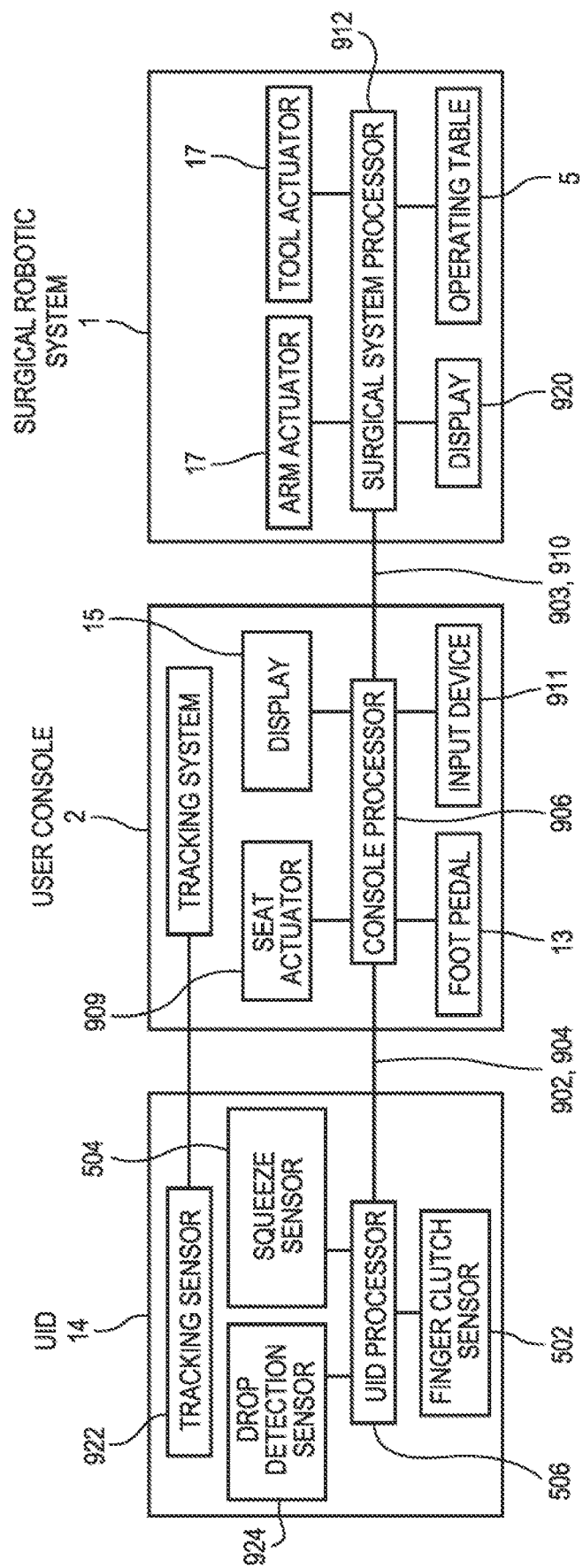
FIG. 9 is a block diagram of a computer portion of a surgical robotic system, in accordance with an embodiment.

Referring now to FIG. 9, FIG. 9 is a block diagram of a computer portion of a surgical robotic system for carrying out the previously discussed operations is shown in accordance with an embodiment. Surgical robotic system 1 can generally include UID(s) 14, user console 2 having computer system 16, and robotic components 104, 112 associated with actuators 17. Computer system 16 and UID 14 have circuitry suited to specific functionality, and thus, the diagrammed circuitry is provided by way of example and not limitation.

One or more processors of user console 2 can control portions of surgical robotic system 1, e.g., surgical robotic arms 112 and/or surgical tools 104. UID 14 may be communicatively coupled to computer system 16 (of user console 2) and/or surgical robotic system 1 to provide input commands that are processed by one or more processors of system 1 to control movement of surgical robotic arm 112 and/or surgical tool 104 mounted on the arm. For example, UID 14 may communicate electrical command signals 902 to computer system 16, e.g., spatial state signals generated by UID processor 606 in response to signals from tracking sensor 922, or clutch signals generated by UID processor 606. The electrical signals may be input commands to cause motion of surgical robotic system 1, or to pause motion of surgical robotic system 1. In addition, the input commands may correspond to the intentional user action(s) indicating a desire to engage and/or disengage the teleoperation mode, which are detected by the UID 14, and the processors of system 1 may use them to engage and/or disengage teleoperation mode as described in reference to FIG. 6-FIG. 8.

The input electrical signals may be transmitted by UID processor 606 to a console processor 906 of computer system 16 via a wired or wireless connection. For example, UID 14 may transmit the command signals 902 to console processor 906 via electrical wire. Alternatively, UID 14 may transmit command signals 902 to console processor 906 via a wireless communication link 904. The wireless communication link may be established by respective RF circuitry of computer system 16 and UID 14. The wireless communication can be via radiofrequency signals, e.g., Wi-Fi or short range signals and/or suitable wireless communication protocols such as Bluetooth.

Console processor 906 of computer system 16 may execute instructions to carry out the different functions and capabilities described above. Instructions executed by console processor(s) 906 of user console 2 may be retrieved from a local memory (not shown), which may include a non-transitory machine-readable medium. The instructions may be in the form of an operating system program having device drivers to control components of surgical robotic system 1, e.g., actuators 17 operatively coupled to surgical robotic arm(s) 112 or surgical tool(s) 104, and/or engage/disengage the teleoperation mode.

In an embodiment, console processor 906 controls components of user console 2. For example, one or more seat actuators 909 can receive commands from console processor 906 to control movement of seat 122. Seat actuator(s) 909 can move seat 122 in one or more degrees of freedom, such as forward/backward, backrest tilt, headrest position, etc., for example, to align seat 122 with the display 15 (to engage teleoperation mode). Console processor 906 can also transmit video data for presentation on display 15. Accordingly, console processor 906 can control operation of user console 2. Input commands to seat actuator(s) 909 or console processor 906 can be entered by the user via foot pedal(s) 13 or another input device 911 such as a keyboard or a joystick.

Console processor 906 can output control signals 903 to other components of surgical robotic system 1 via a link 910. Control signals 903 may be transmitted to control movement of surgical robotic system 1. In an embodiment, computer system 16 is communicatively coupled to downstream components of surgical robotic system 1, e.g., control tower 130, via wired or wireless links. The links can transmit control signals 903 to one or more surgical system processor(s) 912. For example, at least one processor 912 can be located in control tower 130, and may be communicatively coupled to system components, such as surgical robotic platform 5 or one or more displays 920. Actuators 17 of surgical robotic system 1 may receive control signals from surgical system processor 912 to cause movement of arm 112 and/or tool 104 corresponding to movement of UID 14. The control signals can also pause motion of the robotic components by clutching and/or disconnecting an interlock of surgical robotic system 1 when user 107 presses finger clutch 206 or drops UID 14, or can cause the system to engage and/or disengage the teleoperation mode.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. A method for engaging a teleoperation mode of a surgical robotic system, the method comprising:
    receiving a user input from one or more interface devices of the surgical robotic system, wherein the one or more interface devices comprise at least one handheld input device having a finger clutch operable to clutch a first surgical robotic arm and a clutch pedal operable to clutch the first surgical robotic arm and a second surgical robotic arm and the user input comprises a user action on the finger clutch or the clutch pedal;
    receiving a docking input indicating the at least one handheld input device is undocked from a docking station;
    determining, by one or more processors communicatively coupled to the one or more interface devices, whether docking input indicates an intentional engagement of a teleoperation mode in which the first surgical robotic arm or the second surgical robotic arm is controlled by the user input received from the interface devices; and
    in response to determining engagement, transitioning the surgical robotic system into a teleoperation mode.

2. The method of claim 1 wherein the at least one handheld input device is a first handheld input device and the finger clutch is operable to clutch only the first surgical robotic arm.

3. The method of claim 2 further comprising a second handheld input device having a finger clutch operable to clutch only a second surgical robotic arm, and wherein the clutch pedal is operable to simultaneously clutch the first surgical robotic arm and the second surgical robotic arm.

4. The method of claim 1 wherein the user input comprises a tap of the finger clutch over a predetermined interval comprising a predetermined amount of time between the tap of the finger clutch and a subsequent tap of the finger clutch.

5. The method of claim 1 wherein the user input comprises a tap of the clutch pedal over a predetermined interval comprising a predetermined amount of time between the tap of the clutch pedal and a subsequent tap of the clutch pedal.

6. The method of claim 1 wherein a user position input is further received, and the user position input indicates a user is looking toward a display screen, a chair of the surgical robotic system is locked, or the first handheld input device or the second handheld input device is in a workspace of the surgical robotic system.

7. The method of claim 1 wherein the at least one handheld input device comprises a first handheld input device having a first finger clutch and a second handheld input device having a second finger clutch, and the user input comprises a sequence of user inputs comprising a tap of the first finger clutch associated with the first handheld input device and a tap of the second finger clutch associated with the second handheld input device, or a double tap of the first finger clutch or the second finger clutch associated with the first or second handheld input device.

8. The method of claim 1 wherein the at least one handheld input device comprises a first handheld input device and a second handheld input device, and the user input comprises a sequence of user inputs comprising a squeeze of the first and the second handheld input devices, or a double squeeze of the first or second handheld input device.

9. The method of claim 1 wherein the user input comprises a sequence of user inputs and the sequence of user inputs comprises a double tap of the finger clutch and a single tap of the clutch pedal prior to the double tap of the finger clutch.

10. The method of claim 1 wherein the user input indicating an intentional engagement corresponds to a double tap of the clutch pedal, a double tap of the finger clutch, or a single or a double squeeze of the handheld input device at a predetermined interval.

11. The method of claim 1 further comprising:
    providing an alert to a user indicating that the surgical robotic system is transitioning into the teleoperation mode.

12. The method of claim 1 further comprising:
    after transitioning the surgical robotic system into the teleoperation mode determining, by one or more processors communicatively coupled to the one or more interface devices, that the user input indicates an intentional disengagement of the teleoperation mode; and
    in response to determining disengagement, transitioning the surgical robotic system out of the teleoperation mode such that the one or more interface devices are prevented from controlling the first surgical robotic arm or the second surgical robotic arm.

13. A method for disengaging a teleoperation mode of a surgical robotic system, the method comprising:
    receiving a user input from one or more interface devices of the surgical robotic system, wherein the one or more interface devices comprise at least one handheld input device having a finger clutch operable to clutch a first surgical robotic arm and a clutch pedal operable to clutch the first surgical robotic arm and a second surgical robotic arm, and the user input comprises a user action on the finger clutch or the clutch pedal;

receiving a docking input indicating that the at least one handheld input device is in or near a docking station;

determining, by one or more processors communicatively coupled to the one or more interface devices, whether the user input and the docking input indicates an intentional disengagement of a teleoperation mode in which the first surgical robotic arm and the second surgical robotic arm are operable to be controlled by the user input received from the interface devices; and in response to determining disengagement, transitioning the surgical robotic system out of the teleoperation mode such that the one or more interface devices are prevented from controlling the first surgical robotic arm or the second surgical robotic arm.

14. The method of claim 13 wherein the user input comprises a tap of the finger clutch over a predetermined interval comprising a predetermined amount of time between the tap of the finger clutch and a subsequent tap of the finger clutch.

15. The method of claim 13 wherein the user input comprises a tap of the clutch pedal over a predetermined interval comprising a predetermined amount of time between the tap of the clutch pedal and a subsequent tap of the clutch pedal.

16. The method of claim 13 wherein the at least one handheld input device is a first handheld input device and the finger clutch is operable to clutch only the first surgical robotic arm and a second handheld input device comprises a finger clutch operable to clutch only the second surgical robotic arm.

17. The method of claim 13 wherein the docking input comprises detecting by a sensor of the docking station that the at least one handheld input device is positioned in the docking station.

18. The method of claim 13 wherein the handheld input device is a first handheld input device and the user input comprises a sequence of user inputs comprising a tap of the finger clutch associated with the first handheld input device and a tap of a finger clutch associated with a second handheld input device, or a double tap of the finger clutch associated with the first or second handheld input device.

19. The method of claim 13 wherein the user input indicating an intentional disengagement corresponds to pressing and holding the clutch pedal, a double tap of the finger clutch, or a double squeeze of the handheld input device at a predetermined interval.

20. The method of claim 13 further comprising:

determining, by one or more processors communicatively coupled to the one or more interface devices, whether the user input indicates an intentional engagement of the teleoperation mode; and in response to determining engagement, transitioning the surgical robotic system into the teleoperation mode such that the one or more interface devices are operable to control the first surgical robotic arm or the second surgical robotic arm.

\* \* \* \* \*